US009933442B2

(12) United States Patent
Akamatsu et al.

(10) Patent No.: US 9,933,442 B2
(45) Date of Patent: Apr. 3, 2018

(54) MONOCLONAL ANTIBODY FOR ANALYZING HIGH-MOLECULAR WEIGHT ADIPONECTIN AND UTILIZATION OF SAME

(71) Applicants: OTSUKA PHARMACEUTICAL CO., LTD., Tokyo (JP); LSI MEDIENCE CORPORATION, Tokyo (JP)

(72) Inventors: Suguru Akamatsu, Osaka (JP); Kiyonori Katsuragi, Osaka (JP); Hideaki Onishi, Osaka (JP); Midori Abe, Osaka (JP); Toru Hadama, Osaka (JP); Ayako Nishimura, Tokyo (JP); Mio Ooguchi, Tokyo (JP)

(73) Assignee: LSI MEDIENCE CORPORATION, Tokyo (JP)

( * ) Notice: Subject to any disclaimer, the term of this patent is extended or adjusted under 35 U.S.C. 154(b) by 0 days.

(21) Appl. No.: 14/508,993

(22) Filed: Oct. 7, 2014

(65) Prior Publication Data

US 2015/0025226 A1 Jan. 22, 2015

Related U.S. Application Data

(62) Division of application No. 13/319,054, filed as application No. PCT/JP2010/057747 on May 6, 2010, now Pat. No. 8,871,518.

(30) Foreign Application Priority Data

May 7, 2009 (JP) ................................ 2009-112624

(51) Int. Cl.
  *G01N 33/74* (2006.01)
  *C07K 16/26* (2006.01)
  *G01N 33/543* (2006.01)
  *G01N 33/82* (2006.01)
(52) U.S. Cl.
  CPC .............. *G01N 33/74* (2013.01); *C07K 16/26* (2013.01); *G01N 33/543* (2013.01); *G01N 33/54313* (2013.01); *G01N 33/82* (2013.01); *G01N 2800/042* (2013.01)
(58) Field of Classification Search
  None
  See application file for complete search history.

(56) References Cited

U.S. PATENT DOCUMENTS

| 7,067,634 B2 * | 6/2006 | Tomita et al. ............. 530/387.1 |
| 2005/0048565 A1 | 3/2005 | Tomita et al. |
| 2007/0037207 A1 | 2/2007 | Tachikawa et al. |
| 2007/0042424 A1 | 2/2007 | Ebinuma et al. |

FOREIGN PATENT DOCUMENTS

| JP | 3624216 | 12/2004 |
| WO | 2004/086040 A1 | 10/2004 |
| WO | 2005/038457 A1 | 4/2005 |
| WO | 2009/078151 A1 | 6/2009 |

OTHER PUBLICATIONS

Hada et al. "Selective purification and characterization of adiponectin multimer species from human plasma" Biochemical and Biophysical Research Communications 356 (2007) 487-493.*
Schraw et al. "Plasma Adiponectin Complexes Have Distinct Biochemical Characteristics" Endocrinology 2008, 149(5):2270-2282.*
Lonza, "Dulbecco's Phosphate Buffered Saline (DPBS)", 2007, retrieved from http://www.biocenter.hu/pdf/dpbs.pdf on May 1, 2017, one page.*
Kim, "Changes of adiponectin oligomer by moderate weight reduction using phentermine," Yonsei University, 2006, Korea, pp. 1-65.
Komura, N. et al., "Clinical significance of high-molecular weight form of adiponectin in male patients with coronary artery disease," Circ. J., 72(1):23-8, 2008.
Nakano et al.; The novel enzyme-linked immunosorbent assay specific for the high-molecular weight adiponectin; Seikagaku; 2006; 20th IUBMB International Congress of Biochemistry and Molecular Biology and 11th FAOBMB Congress Abstract CD; p. A1153 #3P-B-050.
Nakano, et al.; A novel enzyme-linked immunosorbent assay specific for high-molecular-weight adiponectin; Journal of Lipid Research; 2006; vol. 47, pp. 1572-1582.
Nishimura, et al.; Determination of adiponectin in serum using a latex particle-enhanced turbidimetric immunoassay with an automated analyzer; Clinica Chimica Acta; 2006; vol. 371, pp. 163-168.
Tanita, et al.; Performance of ELISA for specific measurement of High-Molecular-Weight (HMW) adiponectin; Journal of Immunological Methods; 2008; vol. 333, pp. 139-146.

* cited by examiner

*Primary Examiner* — Christine Foster
(74) *Attorney, Agent, or Firm* — Kilpatrick Townsend & Stockton LLP

(57) ABSTRACT

A monoclonal antibody that does not show a crossreactivity with middle-molecular weight (MMW) adiponectin and specifically reacts with high-molecular weight (HMW) adiponectin alone is disclosed. The monoclonal antibody of the present invention can be produced by using HMW adiponectin as an antigen. According to the monoclonal antibody of the present invention, a convenient, high-accurate, and versatile reagent for analyzing HMW adiponectin can be provided.

3 Claims, 6 Drawing Sheets

MONOCLONAL ANTIBODY FOR ANALYZING HIGH-MOLECULAR WEIGHT ADIPONECTIN AND UTILIZATION OF SAME

CROSS-REFERENCE TO RELATED APPLICATIONS

The present application is a division of U.S. application Ser. No. 13/319,054, filed Nov. 4, 2011, now U.S. Pat. No. 8,871,518, which application is a National Stage application under 35 U.S.C. § 371, claiming priority to PCT/JP2010/057747, filed May 6, 2010, which application claims the benefit of priority to Japanese Patent Application No. 2009-112624, filed May 7, 2009, the teachings all of which are incorporated herein by reference in their entirety for all purposes.

TECHNICAL FIELD

The present invention relates to a novel monoclonal antibody specific to high-molecular weight adiponectin, and a method for specifically analyzing (in particular, measuring) the high-molecular weight adiponectin using the monoclonal antibody.

BACKGROUND ART

Adiponectin is a secretory protein that is specifically expressed in adipocytes, and was reported to exhibit an anti-arteriosclerotic effect and an insulin resistance-reducing effect. In recent years, adiponectin has been reported to be involved in cancer, inflammation, and metabolic syndrome, and is considered to function as a defensive factor in the living body. Human adiponectin consists of 244 amino acid residues, and is known to have a molecular weight of approximately 28 kDa as a monomer. It was confirmed that adiponectin is present in blood in forms of a trimer (LMW: Low-molecular weight) as the basic structure, a hexamer (MMW: Middle-molecular weight) composed of the trimer, and multimers (HMW: High-molecular weight) composed of one or more LMWs and/or MMWs.

These various forms of adiponectin exhibit different physiological effects. For example, it was reported that HMW and MMW activated NF-κB in a C2C12 cell line, but LMW did not. Further, it was reported that persons deficient in adiponectin secretion could not produce HMW adiponectin and suffered hypoadiponectinemia and diabetes, and that the content ratio of HMW adiponectin was decreased in patients with coronary artery disease in comparison with healthy persons. Furthermore, it was reported that adiponectin of which the blood level changed before and after a diet was HMW. Therefore, it is important to detect HMW adiponectin alone in studies of adiponectin and various diseases.

In general, a protein molecule can be detected using a monoclonal antibody that specifically recognizes the protein as an antigen. However, in the case that the antigen is a mixture of multimers in various forms composed of single monomers such as adiponectin, it is difficult to obtain an antibody specific to only a molecule having a specific size. Because an antibody usually recognizes a primary amino acid sequence of an antigen, when an antigen is multimers, the antibody generally recognizes a primary amino acid sequence of the monomer that forms the multimers. Because adiponectin is composed of single monomers, an antibody that recognizes the adiponectin monomer simultaneously recognizes adiponectin multimers in any form. Even if a monoclonal antibody recognizes a tertiary structure, the crossreactivity to other molecules cannot be avoided in a molecule such as HMW adiponectin in which many basic structures are polymerized.

Therefore, in a case of using a general antibody, it is difficult to detect an adiponectin molecule having a specific size alone.

To quantitatively determine adiponectin having a specific molecular size, as conventional methods, a method in which adiponectin is pretreated (for example, gel filtration) to fractionate it based on its molecular weight and each peak is detected, and a method in which a specific molecule(s) is digested and the remaining molecule is detected, are generally used. Further, an ELISA technique that does not need pretreatment, such as gel filtration or a protease treatment, was developed, but crossreactivity to MMW is observed, and the ELISA technique is not specific to HMW. Therefore, a technique capable of detecting adiponectin having a specific molecular size alone, by a simple pretreatment or without pretreatment, is desired.

As conventional methods for measuring adiponectin having a specific molecular size, in addition to the above-mentioned gel filtration method, the following two methods are known:
(1) a method in which a pretreatment with an enzyme that digests LMW and MMW is carried out, and the remaining adiponectin that is not digested by the enzyme is measured to detect HMW alone (Patent literature 1), and
(2) a method in which an antibody that does not react with the adiponectin monomer, but recognizes a trimer and/or its associating molecule, high-molecular weight adiponectin, is used to detect the high-molecular weight adiponectin antigen alone (Patent literature 2).

However, the pretreatment with the enzyme needs an enzyme treatment time of several tens of minutes. In addition, in the case of incubation for a long time that exceeds an optimum time, there is a possibility that the target molecule per se may be digested by a coexisting protease, and thus, it is necessary to strictly select the incubation time. Further, in the treatment with an enzyme, an optimum digestive enzyme should be selected in accordance with the type of a target antigen, and thus, it is not a versatile method.

In the case of using the conventional antibody that recognizes high-molecular weight adiponectin, not only high-molecular weight adiponectin (HMW) but also other multimers (LMW and MMW) are simultaneously recognized, and thus, it is not a method capable of specifically detecting HMW alone. An antibody that specifically recognizes HMW adiponectin alone is unknown.

CITATION LIST

Patent Literature

[Patent literature 1] WO2005/038457
[Patent literature 2] Japanese Patent No. 3624216

SUMMARY OF INVENTION

Technical Problem

In the conventional ELISA for detecting HMW without pretreatment, there is the problem that the crossreactivity to MMW is observed in a sample containing a high level of MMW, and the HMW-specific measurement was indeed difficult. In addition, even if an antibody shows a high selectivity to HMW in ELISA, the antibody sometimes lose the HMW selectivity by latex labeling, and thus, it was very difficult to easily measure HMW adiponectin using latex. An object of the present invention is to provide a monoclonal antibody for selectively detecting or quantitatively determining HMW adiponectin alone, without showing crossreactivity to MMW adiponectin, and a convenient, highly-accurate, and versatile reagent for analyzing high-molecular weight adiponectin.

Solution to Problem

The present inventors constructed a latex reagent for analyzing high-molecular weight adiponectin capable of more conveniently and selectively detecting or quantitatively determining HMW adiponectin alone, and screened for a monoclonal antibody used in the latex reagent. As a result, it was confirmed that even when an antibody that showed a relatively high specificity to HMW in a sandwich ELISA system was used, the antibody did not show the HMW specificity at all when it was evaluated as a latex reagent, and thus, the present inventors produced a novel monoclonal antibody using the HMW fraction alone of adiponectin in human blood. The present inventors confirmed that this monoclonal antibody had similar reactivities in Western blotting analysis, compared to monoclonal antibodies prepared using recombinant adiponectin expressed in *E. coli*, but showed an extremely high HMW specificity when evaluated by a sandwich ELISA system. Further, the present inventors constructed a latex reagent for analyzing adiponectin using the monoclonal antibody, and found that HMW adiponectin could be selectively measured using the latex reagent without crossreactivity to MMW, and completed the present invention.

The present invention relates to:
[1] a monoclonal antibody characterized by specifically reacting with high-molecular weight adiponectin,
[2] a method for producing the monoclonal antibody of [1], characterized by using high-molecular weight adiponectin as an antigen,
[3] a method for immunologically analyzing high-molecular weight adiponectin, characterized by using the monoclonal antibody of [1],
[4] the method of [3], wherein the method is a latex agglutination method,
[5] a reagent for immunologically analyzing high-molecular weight adiponectin, comprising the monoclonal antibody of [1], and
[6] the reagent according to claim 5, comprising latex particles carrying the monoclonal antibody of [1].

Advantageous Effects of Invention

According to the novel monoclonal antibody of the present invention, a more convenient and accurate reagent (in particular, a latex reagent) and method for analyzing the high-molecular weight (HMW) adiponectin capable of selectively analyzing (detecting or quantitatively measuring) the high-molecular weight adiponectin alone can be provided.

DESCRIPTION OF EMBODIMENTS

Figure 1:
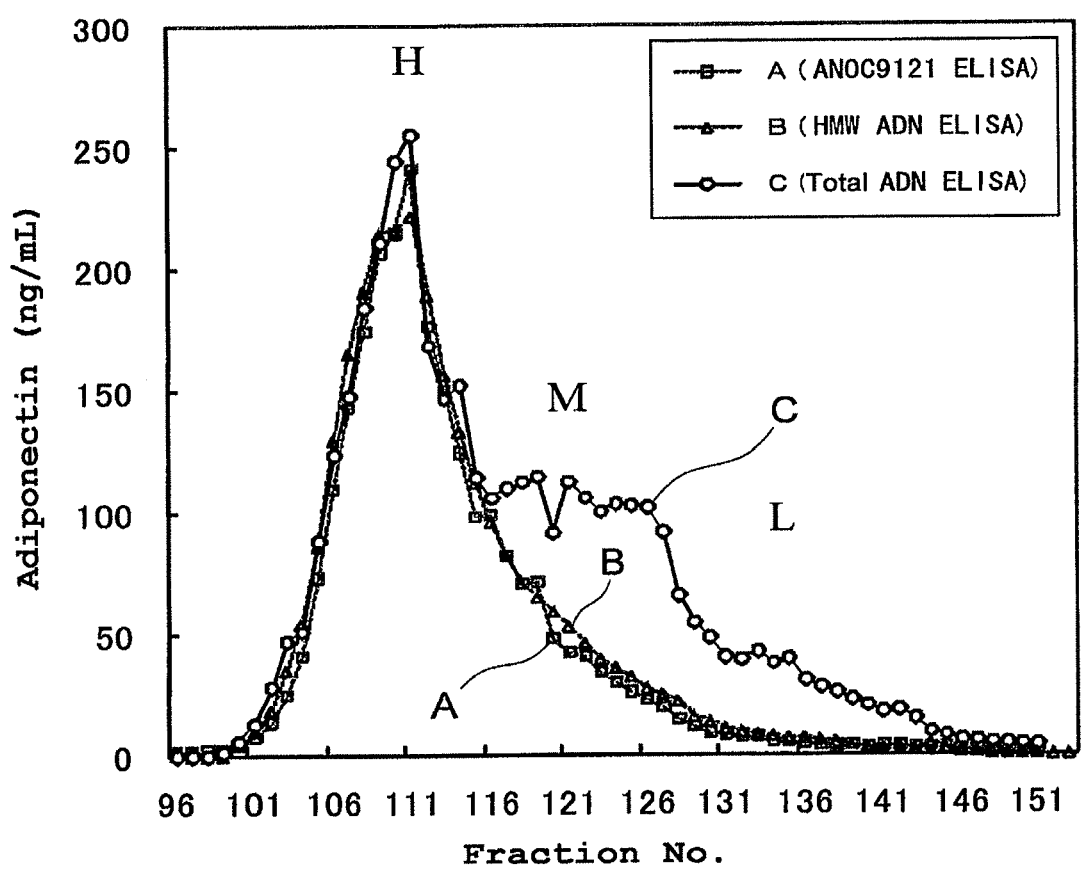
FIG. 1 is a graph showing the results obtained by measuring the amount of adiponectin contained in gel filtration fractions of a human serum sample (showing a low level of MMW) using various ELISA kits using known monoclonal antibodies.

The monoclonal antibody of the present invention specifically reacts with high-molecular weight adiponectin. The wording "specifically react with high-molecular weight adiponectin" as used herein means that it reacts with high-molecular weight adiponectin, does not react with trimeric adiponectin, and does not substantially react with hexameric adiponectin. The high-molecular weight adiponectin, the trimeric adiponectin, and the hexameric adiponectin are sometimes referred to as HMW adiponectin, MMW adiponectin, and LMW adiponectin (or simply referred to as HMW, MMW, and LMW), respectively.

The term "high-molecular weight adiponectin" as used herein means multimers of which the basic structure is a polymer of LMW and/or MMW, and which are fractionated under nondenaturing conditions into fractions of approximately 440 kDa or more (i.e., the boundary between HMW and MMW is approximately 440 kDa) with a peak around 670 kDa.

These molecular weights are values determined by gel filtration carried out in Comparative Examples and Examples described below, and the conditions for the gel filtration are as follows:

Column: SUPERDEX® 200 prep grade (GE Healthcare Bioscience), which column is a gel filtration column having cross-linked agarose and dextran media
Mobile phase (solvent): D-PBS
Pumping speed: 1 mL/min
Molecular weight markers:
(1) bovine serum albumin: 67,000 (da)
(2) aldolase: 158,000
(3) catalase: 232,000
(4) ferritin: 440,000
(5) thyroglobulin: 669,000
(6) Blue Dextran 2000: 2,000,000

The wording "not substantially react with hexameric adiponectin (MMW)" as used herein means that it does not react with molecules having a peak around 400 kDa and eluted between approximately 250 to 440 kDa by fractionating a human serum under nondenaturing conditions.

The antibody specific to HMW adiponectin of the present invention may be prepared in accordance with a conventional method for preparing monoclonal antibodies, except that adiponectin that is directly collected from a living body and fractionated into HMW is used as an antigen.

The biological sample derived from a living body and used as the antigen is not particularly limited, so long as it is a biological liquid suspected of containing HMW adiponectin. Examples of the sample include a biological fluid (for example, blood (i.e., whole blood), serum, plasma, urine, cerebrospinal fluid, or secretory fluids) directly collected from a living body, and a biological material-derived liquid (for example, various extracts of organs, tissues, or cells, or various culture liquids of tissues or cells) obtained by treating biological materials (for example, organs, tissues, or cells) collected from a living body.

A HMW adiponectin fraction as the antigen may be prepared by fractionating the biological sample into a fraction containing adiponectin with various molecular weights including HMW adiponectin, and separating HMW adiponectin from the fraction by gel filtration chromatography. The fraction containing adiponectin with various molecular weights including HMW adiponectin may be obtained by affinity chromatography immobilized with an antibody that recognizes HMW adiponectin. The antibody to be immobilized is not particularly limited, so long as it can recognize at least HMW adiponectin, and an antibody that recognizes MMW and/or LMW adiponectin may be used. Affinity chromatography or gel filtration chromatography may be appropriately carried out in accordance with an antibody used, the amount of a biological sample, and the like. Affinity chromatography may be carried out after the separation by gel filtration chromatography.

The obtained HMW adiponectin monoclonal antibody may be used in a method for selectively measuring HMW adiponectin, as an immunoglobulin molecule per se, or as an antibody fragment (for example, Fab, Fab', F(ab')$_2$, or Fv), which may be prepared in accordance with a conventional method.

The assay sample to be analyzed by the present invention is not particular limited, so long as it is a biological liquid suspected of containing HMW adiponectin. Examples of the sample include a biological fluid (for example, blood (i.e., whole blood), serum, plasma, urine, cerebrospinal fluid, or secretory fluids) directly collected from a living body, and a biological material-derived liquid (for example, various extracts of organs, tissues, or cells, or various culture liquids of tissues or cells) obtained by treating biological materials (for example, organs, tissues, or cells) collected from a living body.

HMW adiponectin is present, for example, at a concentration of 1 μg/mL to several tens of μg/mL in normal human blood. Alternatively, the concentration of HMW adiponectin contained in a biological material-derived liquid may be adjusted to 1 μg/mL to several tens of μg/mL, by appropriately determining the amount of a treating liquid (for example, a solution for extraction or a solution for cultivation) from a pilot test or the like.

As above, a biological liquid (in particular, blood) to be analyzed by the present invention contains HMW adiponectin at a concentration of 1 μg/mL to several tens of μg/mL, and thus, may be analyzed, without predilution, by the reagent of the present invention for analyzing HMW adiponectin.

As the method for analyzing HMW adiponectin of the present invention, conventional immunological measuring methods may be used. Examples of the immunological measuring method include an ELISA method, an RIA method, an agglutination method, and an immunochromatography method. Hereinafter, an agglutination method using latex will be explained more particularly.

As latex particles used in the present invention, conventional latex particles, such as latex particles made of polystyrene, a styrene-styrene sulfonate copolymer, or the like, may be used. The average particle size of latex particles carrying the antibody specific to HMW adiponectin may be appropriately selected from the range of 0.05 to 1.0 μm in general, in accordance with, for example, the type of a biological fluid used as a sample, the concentration of HMW adiponectin contained, or the measuring apparatus.

For example, in a case of analyzing HMW adiponectin in blood, since HMW adiponectin is present in a normal human sample at a high concentration of 1 μg/mL to several tens of μg/mL, the measuring range of an assay system for HMW adiponectin in blood can be guaranteed by appropriately selecting the particle size of latex. More particularly, when the particle size is 0.1 μm or less, the accuracy in measuring concentrations of 5 μg/mL or less that are clinically significant is sometimes not guaranteed. When the particle size is 0.5 μm or more, a normal sample with a high level can sometimes not be measured. Therefore, as the assay system for HMW adiponectin in blood, latex particles having an average particle size of 0.1 to 0.5 μm are preferable.

The latex reagent for analyzing HMW adiponectin of the present invention may be in any form, so long as it contains a suspension liquid of latex particles carrying the monoclonal antibody specific to HMW adiponectin. The latex reagent may be in various forms, for example, a one-liquid-component reagent containing a buffer and latex particles sensitized with the antibody specific to HMW adiponectin; a two-liquid-component reagent composed of a buffer as the first reagent component and latex particles sensitized with the antibody specific to HMW adiponectin as the second reagent component; or the like.

In the method for analyzing HMW adiponectin of the present invention, a biological fluid suspected of containing adiponectin may be collected; the obtained biological fluid may be regarded as a sample without predilution and/or pretreatment (i.e., while being maintained in the original state), or alternatively, the obtained sample may be appropriately treated to prepare a sample; and the sample may be brought into contact with the suspension liquid of latex particles carrying the antibody specific to HMW adiponectin of the present invention (preferably the latex reagent for analyzing HMW adiponectin of the present invention).

For example, a preferred embodiment of the method of the present invention, a method for analyzing HMW adiponectin using an automated analyzing apparatus, includes:
(1) collecting a biological fluid suspected of containing adiponectin; and
(2) preparing a sample from the biological fluid obtained in the previous step by maintaining the original state, or by carrying out an appropriate predilution and/or pretreatment, bringing the sample into contact with a suspension liquid of latex particles carrying an antibody specific to HMW adiponectin in an automated analyzing apparatus, and optically analyzing the degree of agglutination of the latex particles.

In the case that HMW adiponectin contained in various biological fluids, such as blood, is measured using a conventional measuring method such as a radioimmunoassay or an enzyme immunoassay, for example, a step of diluting a sample 500 to 5000-fold is needed. By contrast, in the method for analyzing HMW adiponectin of the present invention, a latex agglutination reaction can be carried out using an original biological fluid as a sample, without predilution or pretreatment of the biological fluid, for example, by appropriately selecting the particle size of latex particles (for example, in a case of HMW adiponectin in blood, a particle size of 0.1 to 0.5 μm is preferable).

In the method for analyzing HMW adiponectin of the present invention, an agglutination reaction is carried out using latex particles carrying an antibody specific to HMW adiponectin (for example, the latex reagent for analyzing HMW adiponectin of the present invention), and the degree of agglutination generated is optically analyzed (in particular, measured) to analyze (in particular, measure) the amount of HMW adiponectin contained in a biological fluid (for example, blood). The degree of agglutination of latex particles may be optically analyzed, for example, by visual observation, or using an optical device for measuring scattered light intensity, absorbance, or transmitted light intensity. The measuring wavelength is preferably 300 to 800 nm. The measurement may be carried out, in accordance with a conventional method, by selecting the average particle size or the concentration of latex particles used, or a reaction time, and measuring an increase or a decrease in scattered light intensity, absorbance, or transmitted light intensity. These methods may be used in an appropriate combination thereof.

In general, the concentration of the latex sensitized with an antibody specific to HMW adiponectin, which is contained in the system for measuring a latex agglutination reaction, may be appropriately selected in accordance with the concentration of a coexisting additive, such as salts, proteins, or sugars. In general, as the concentration in the final liquid volume of the reaction system, the latex sensitized with an antibody specific to HMW adiponectin may be adjusted to preferably 0.05 to 10 mg/mL, more preferably 0.1 to 2 mg/mL. When the concentration of the latex sensitized with an antibody specific to HMW adiponectin is too low, the measurement of an agglutination reaction at a low level is sometimes difficult, and when it is too high, the measurement of an agglutination reaction at a high level is sometimes difficult, and the reproducibility sometimes becomes poor.

In the present invention, the agglutination reaction of latex particles can be measured more accurately, and the measurable range in a low level area and a high level area can be further expanded, by controlling other factors that influence the agglutination reaction of the latex sensitized with an antibody specific to HMW adiponectin. Examples of the other factors that influence the latex agglutination reaction include the concentration of the latex particles, the amount of the antibody sensitized on the latex particles, and the particle size of the latex particles.

The conditions for the latex agglutination reaction in the method for analyzing HMW adiponectin of the present invention may be the ordinary conditions, and various buffers may be approximately selected as a reaction medium in accordance with the analysis for HMW adiponectin in various biological fluids. In the case of analyzing HMW adiponectin in blood, the buffer is not particularly limited, so long as it has an ion strength and pH that do not inactivate HMW adiponectin in blood and that do not inhibit the latex agglutination reaction. Examples of the buffer include Good's buffers, a glycine buffer, and a Tris buffer. The pH in the reaction is preferably 5 to 10, more preferably 6 to 8.

The reaction temperature is preferably 0 to 50° C., more particularly 20 to 40° C. The reaction time may be appropriately selected.

EXAMPLES

The present invention now will be further illustrated by, but is by no means limited to, the following Examples.

Comparative Example 1

Conventional Monoclonal Antibodies

For comparison with the monoclonal antibody of the present invention, two monoclonal antibodies ANOC9121 and Clone5A, which was prepared by immunizing mice with a recombinant adiponectin antigen expressed in E. coli, were used as conventional monoclonal antibodies. The reactivities of these monoclonal antibodies against human adiponectin in blood are summarized in Table I. Both antibodies were able to equally detect MMW and HMW in blood by Western blotting under nonreduced conditions. However, in sandwich ELISAs using a single antibody, Clone5A recognized all molecules in blood, and ANOC9121 slightly crossreacted with MMW.

TABLE 1

| | Western blotting | | Sandwich ELISA |
| --- | --- | --- | --- |
| Antibody | Reduced | Nonreduced | using single antibody |
| ANOC9121 | Monomer was detected | MMW and larger molecules were detected | High specific to HMW Slightly crossreacted with MMW |
| Clone5A | Not reacted | MMW and larger molecules were detected | All molecules were detected |

Problems of Conventional Monoclonal Antibodies (1): Crossreactivity with MMW

The previously prepared sandwich ELISA kit using ANOC9121 alone, and a commercially available high-molecular weight adiponectin ELISA kit (FUJIREBIO Inc.), which does not need pretreatment, were used to measure gel filtration fractions from two human sera. Total adiponectin was measured using a human adiponectin ELISA kit (Otsuka Pharmaceutical Co., Ltd.).

Unless otherwise specified, the conditions for gel filtration carried out in the Comparative Examples and Examples of the specification are as follows:
Column: SUPERDEX® 200 prep grade (GE Healthcare Bioscience)), which column is a gel filtration column having cross-linked agarose and dextran media
Mobile phase (solvent): D-PBS
Pumping speed: 1 mL/min
Molecular Weight Markers:
(1) bovine serum albumin: 67,000 (da)
(2) aldolase: 158,000
(3) catalase: 232,000
(4) ferritin: 440,000
(5) thyroglobulin: 669,000
(6) Blue Dextran 2000: 2,000,000

Figure 2:
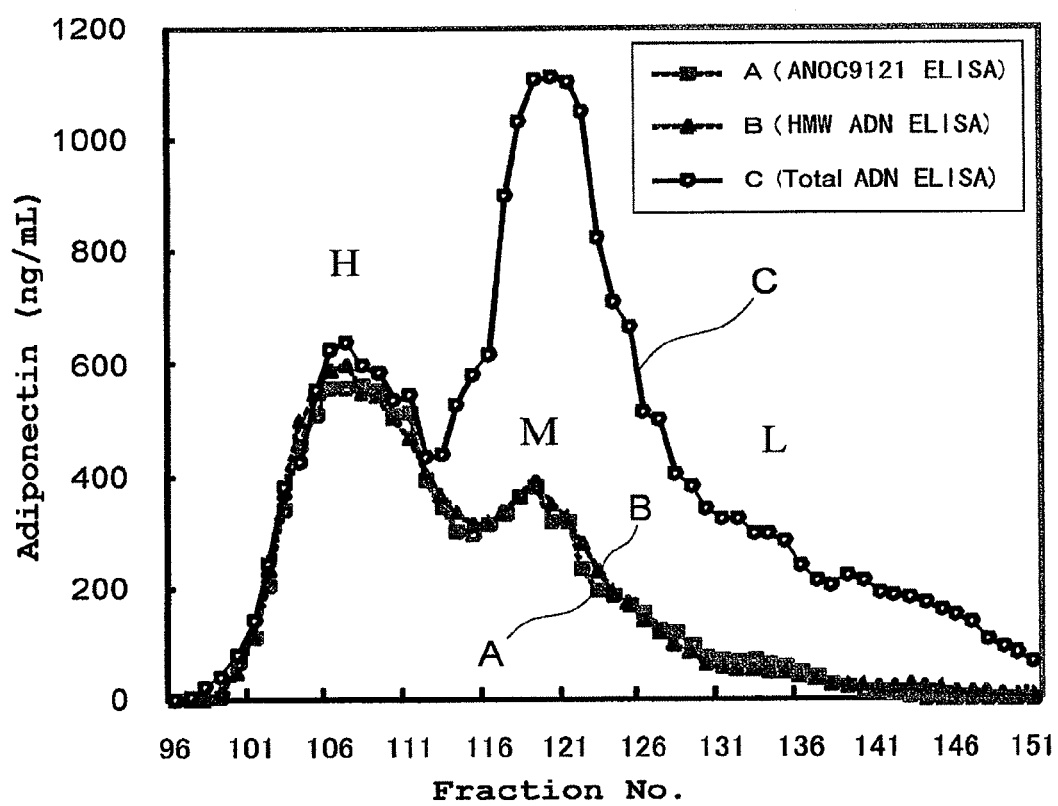
FIG. 2 is a graph showing the results obtained by measuring the amount of adiponectin contained in gel filtration fractions of a human serum sample (showing a high level of MMW) using the same ELISA kits as those used in FIG. 1.

The results obtained by using a serum sample with a low content ratio of MMW are shown in FIG. 1, and the results obtained by using a serum sample with a high content ratio of MMW are shown in FIG. 2. In FIG. 1 and FIG. 2, A shows the results of the sandwich ELISA using ANOC9121, B shows the results of the commercially available high-molecular weight adiponectin ELISA kit (FUJIREBIO Inc.), and C shows the results of the human adiponectin ELISA kit (Otsuka Pharmaceutical Co., Ltd.) for measuring total adiponectin.

As a result, both the ANOC9121 ELISA kit and the commercially available high-molecular weight adiponectin ELISA kit were able to specifically measure the high-molecular weight adiponectin (H), in the case of the sample with a low level of MMW as shown in FIG. 1. By contrast, the crossreactivity with MMW was observed in both the kits, in the case of the sample with a high level of MMW as shown in FIG. 2, and this result indicates the difficulty of a specific measurement of HMW.

In this regard, the HMW fraction, the MMW fraction, and the LMW fraction are, respectively: a fraction with molecular weights higher than approximately 440 kDa, a fraction with molecular weights between 250 kDa and 440 kDa, and a fraction with molecular weights lower than approximately 250 kDa, under the above-mentioned gel filtration conditions.

Comparative Example 2

Problems of Conventional Monoclonal Antibodies (2): Problem in Preparing Latex Reagent Monoclonal antibody ANOC9121, which has a reactivity to MMW and a high specificity for HMW in ELISA, was used to attempt to prepare a latex reagent.

(1) Preparation of Latex Reagent Sensitized with Monoclonal Antibody ANOC9121

To 9 mL of a liquid that was prepared by dissolving monoclonal antibody ANOC9121 at a concentration of 0.5 mg/mL in a 0.01 mol/L Tris buffer (pH 8.0), 1 mL of polystyrene latex (solid content: 10 wt %) having an average particle size of 0.2 μm was added, and stirred at room temperature for 60 min. A Tris buffer (pH 8.0) containing 0.5 wt % of bovine serum albumin was further added to the liquid, and the mixture was stirred at room temperature for 60 min, and centrifuged at 20000 rpm. The latex was suspended by adding 10 mL of a Tris buffer (pH 8.0) to the obtained precipitate, to prepare a liquid containing latex sensitized with monoclonal antibody ANOC9121.

(2) Preparation of Buffer

A buffer was prepared by adding sodium chloride at a concentration of 0.9% (wt %) to a 0.1 mol/L Tris buffer (pH8.0) containing bovine serum albumin at a concentration of 0.5% (wt %).

(3) Latex Reagent for Analyzing HMW Adiponectin

A reagent for measuring a human adiponectin antigen used in this Comparative Example was prepared as a two-liquid-component reagent composed of the buffer prepared in (2) as the first reagent and the latex sensitized with monoclonal antibody ANOC9121 prepared in (1) as the second reagent.

Measurement of Adiponectin (1) Measurement of Adiponectin Fractions

To 35 μL of adiponectin fractions from a human serum (a sample with a low level of MMW), 90 μL of the buffer prepared in (2) was added, and the mixtures were allowed to stand at 37° C. for a predetermined period of time. To each of the mixtures, 90 μL of the liquid containing latex sensitized with monoclonal antibody ANOC9121 prepared in (1) was further added and stirred. After 5 min. had passed, the absorbance at a wavelength of 570 nm was measured. A variation in absorbance during this period is regarded as the variation in absorbance (ΔAbs). A standard adiponectin antigen liquid was used to prepare a calibration curve, based on the ΔAbs values and the antigen concentrations. The adiponectin value was calculated from the ΔAbs of each fraction sample using this calibration curve. This measurement was carried out using a HITACHI automated analyzer type 7170.

Simultaneously with this measurement, total adiponectin was measured using a commercially available human adiponectin latex kit (Mitsubishi Kagaku Iatron, Inc.). With respect to the absorbance values measured, for the comparison between the peaks obtained by both reagents, the absorbance values measured using the latex reagent sensitized with monoclonal antibody ANOC9121 were compensated so that the absorbance values from the No. 109 fraction accorded with each other.

Figure 3:
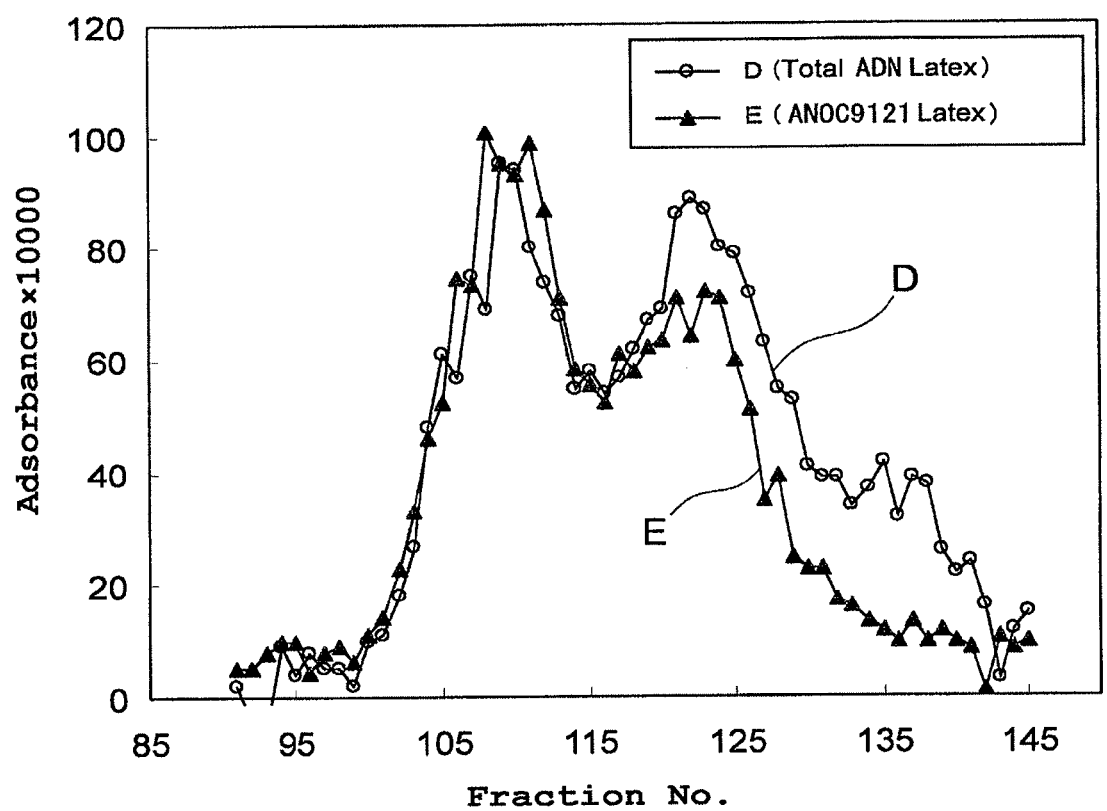
FIG. 3 is a graph showing the results obtained by measuring the amount of adiponectin contained in gel filtration fractions of a human serum sample, using a latex reagent prepared using the known monoclonal antibody ANOC9121.

The results of the evaluation for adiponectin fractions from a human serum using the latex reagent containing ANOC9121 for analyzing HMW adiponectin are shown in FIG. 3 (E in FIG. 3).

From the comparison with the results of the commercially available latex reagent for analyzing total adiponectin (D in FIG. 3), it was found that the latex reagent using ANOC9121 for analyzing adiponectin did not react with the fractions corresponding to LMW, but reacted with HMW and MMW like the latex reagent for analyzing total adiponectin. This result shows that the latex reagent using ANOC9121 reacts with MMW even in the case of a sample with a low level of MMW, and the same performance as that of the ELISA could not be attained.

As a reason that the latex reagent did not exhibit the same performance as that of the ELISA, it is considered to be caused by the difference in reaction mechanisms, that is to say, the first antibody is reacted, and then, the second antibody is reacted in ELISA, whereas agglutination simultaneously starts in a latex reagent. It is further considered to be caused by a low specificity and a low affinity for HMW.

Example 1

(1) Preparation of Immunogen and Novel Monoclonal Antibody

The inventors concluded that it was difficult to obtain a monoclonal antibody with a high specificity for HMW by the previously attempted antibody production method using a recombinant adiponectin expressed in *E. coli*, and thus, the HMW fraction alone was isolated from adiponectin in human blood, and was used to prepare the monoclonal antibody. Total adiponectin in human blood was purified using an above-mentioned ANOC9121-bound column. This column was prepared by coupling 3 to 10 mg/mL of purified ANOC9121 with 4 g of CNBr-activated Sepharose 4B. The column was washed with a phosphate buffer, and 5 to 20 mL of a human serum was applied to the column. The column was washed with a phosphate buffer to remove excess serum components, and human adiponectin in blood was eluted from the column with an eluent. As the eluent, a protein denaturing agent such as several mol/L urea, a chaotropic ion, or a several mol/L sodium chloride solution may be used, and 6 mol/L urea was used in this Example. The eluted adiponectin was further applied to gel filtration purification to purify the HMW of human adiponectin in blood by collecting, not all fractions containing HMW, but the early fractions alone before the HMW peak, i.e., only fractions having molecular weights higher than that of the HMW peak.

The purified human HMW adiponectin in blood was used, together with Freund's complete adjuvant or Freund's incomplete adjuvant, to immunize Balb/C mice in an amount of 1 to 10 μg/body several times every other week.

The spleens were removed from the mice, and the spleen cells were fused with mouse myeloma cell line P3U1 by the polyethylene glycol method, in accordance with a conventional method, to produce hybridomas.

To screen obtained hybridomas for a monoclonal antibody with a high specificity for more native adiponectin, adiponectin contained in blood was used as adiponectin that was not denatured at all. More particularly, the Fc portion of ANOC9121 was digested to prepare ANOC9121 F(ab')$_2$, and a plate to which ANOC9121 F(ab')$_2$ was immobilized was prepared. To this F(ab')$_2$ plate, a human serum that had been appropriately diluted was reacted, and then, the culture supernatants of the hybridomas were reacted. An anti-mouse IgG Fc antibody labeled with horse radish peroxidase (HRP) was further added to the plate, and the plate was incubated. After the incubation, the strength of development of 3,3',5, 5'-tetramethylbenzidine was measured to obtain mouse-mouse hybridoma Clone8D that produced monoclonal antibody Clone8D having a high specificity and a high affinity for native adiponectin.

(2) Evaluation for Newly Produced Monoclonal Antibody by Western Blotting

The anti-human adiponectin monoclonal antibody Clone8D, which was prepared using the HMW adiponectin fraction purified from blood, was used to analyze adiponectin in human blood by Western blotting. As samples, human blood was electrophoresed under nonreduced and unheated conditions and under reduced conditions with 2-mercaptoethanol, and these samples were reacted with the above-mentioned three antibodies ANOC9121, Clone5A, and Clone8D, and were stained. Human adiponectin in blood is present in various forms such as HMW, MMW, and LMW under nonreduced and unheated conditions, but under reduced condition, the trimer and higher multimers disappear and adiponectin is present in the monomer form with approximately 28,000 Da or as a molecule corresponding to the dimer. Monoclonal antibody ANOC9121 recognized all of these forms under nonreduced and unheated conditions and under reduced conditions. By contrast, monoclonal antibody Clone5A, and monoclonal antibody Clone8D prepared using human adiponectin in blood did not recognize the monomer denatured by reduction, but recognized a plurality of macromolecules under nonreduced and unheated conditions. However, so long as it was evaluated by Western blotting, significant differences were not observed among the three monoclonal antibodies with respect to reactivity to the macromolecules.

Example 2

Evaluation of Newly Produced Monoclonal Antibody by ELISA

A sandwich ELISA using Clone8D was constructed, and compared with conventional sandwich ELISAs with respect to their HMW specificity. More particularly, Clone8D that had been diluted to a concentration of 5 to 10 µg/mL with a phosphate buffer was added to a commercially available 96-well ELISA plate, and an immobilization reaction was carried out overnight. This antibody-immobilized plate was blocked with a phosphate buffer containing 0.1 to 1% bovine serum albumin. In the antibody-immobilized plate, human serum fractions that had been HPLC-fractionated using a SUPERDEX® 200 column (GE Healthcare, which column is a gel filtration column having cross-linked agarose and dextran media) were reacted, and after washing, Clone8D labeled with biotin was reacted. HRP-conjugated streptavidin was further added to the plate, and the plate was incubated. After the incubation, excess HRP-conjugated streptavidin was removed by washing. The strength of development obtained by the addition of 3,3',5,5'-tetramethylbenzidine was measured to determine the amount of adiponectin in each fraction.

Further, the same fractions were measured using the ELISA kits used in Comparative Example 1, i.e., the sandwich ELISA kit using ANOC9121 alone, and the commercially available high-molecular weight adiponectin ELISA kit (FUJIREBIO Inc.) that does not need pretreatment, to confirm the crossreactivity with HMW. Furthermore, the human adiponectin ELISA kit (Otsuka Pharmaceutical Co., Ltd.) was used to measure total adiponectin.

Figure 4:
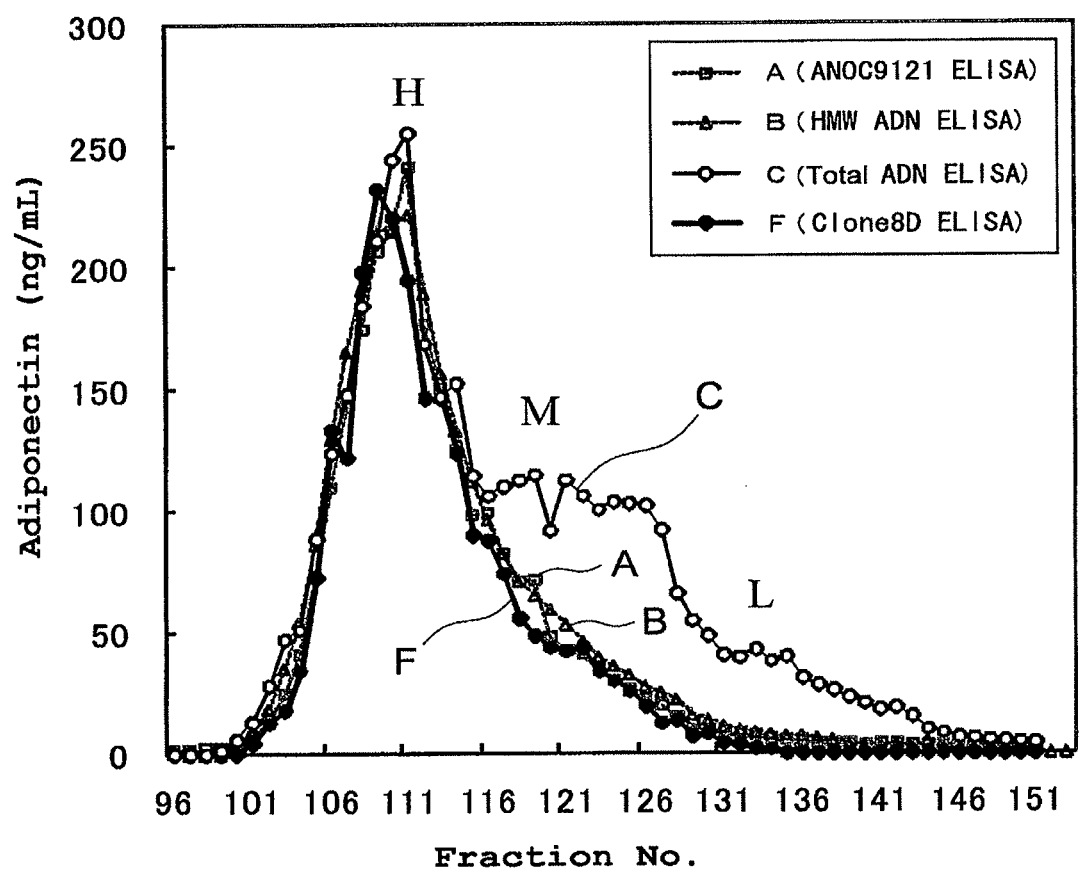
FIG. 4 is a graph showing the results obtained by measuring the amount of adiponectin contained in gel filtration fractions of a human serum sample (showing a low level of MMW) using the ELISA kit of the present invention as well as the same ELISA kits as those used in FIG. 1.
Figure 5:
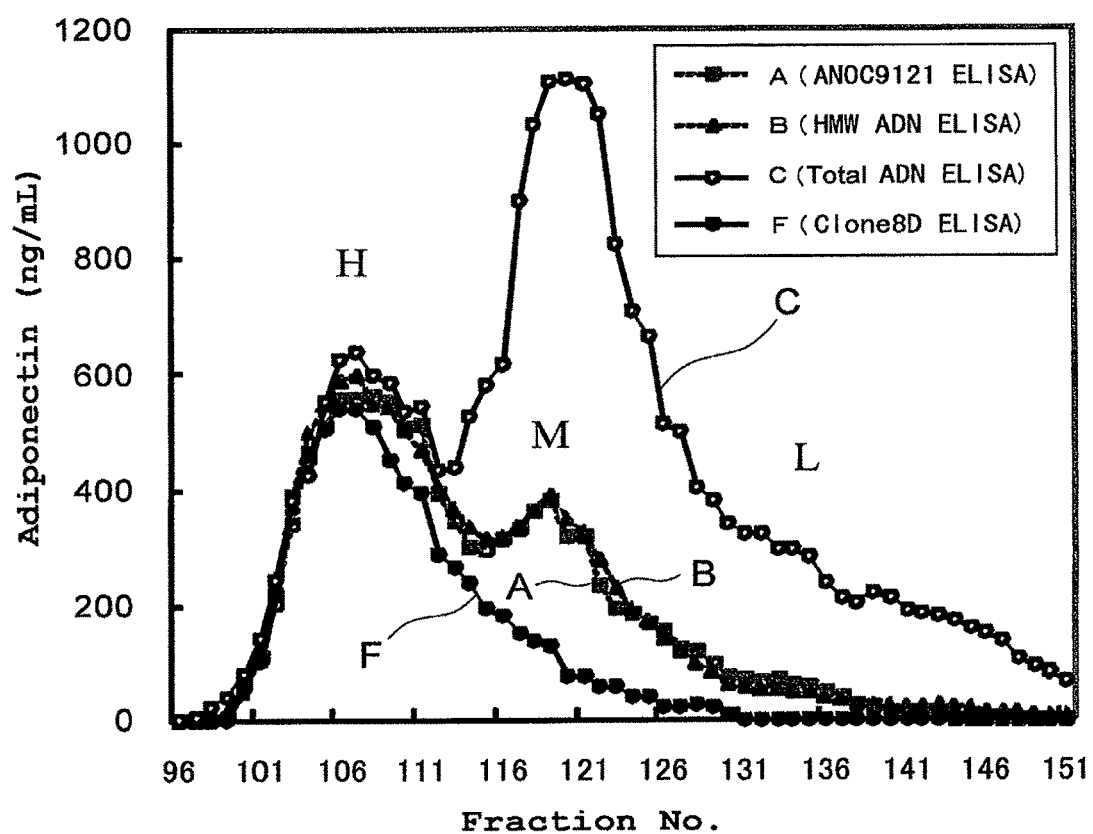
FIG. 5 is a graph showing the results obtained by measuring the amount of adiponectin contained in gel filtration fractions of a human serum sample (showing a high level of MMW) using the same ELISA kits as those used in FIG. 4.

The results are shown in FIG. 4 and FIG. 5 The sandwich ELISA using Clone8D (F in FIG. 4 and FIG. 5) was able to carry out a HMW-specific measurement without crossreactivity with MMW, not only in the case of a sample with a low level of MMW as shown in FIG. 4, but also in the case of a sample with a high level of MMW as shown in FIG. 5, in contrast to the other ELISA methods.

Example 3

Preparation of Latex Reagent for Analyzing High-Molecular Weight Adiponectin Using Novel Monoclonal Antibody (1) Preparation of Reagent Containing Latex Sensitized with Monoclonal Antibody Clone8D To 9 mL of a liquid that was prepared by dissolving monoclonal antibody Clone8D at a concentration of 0.5 mg/mL in a 0.01 mol/L Tris buffer (pH 8.0), 1 mL of polystyrene latex (solid content: 10 wt %) having an average particle size of 0.2 µm was added, and stirred at room temperature for 60 min. A Tris buffer (pH 8.0) containing 0.5 wt % of bovine serum albumin was further added to the liquid, and the mixture was stirred at room temperature for 60 min, and centrifuged at 20000 rpm. The latex was suspended by adding 10 mL of a Tris buffer (pH 8.0) to the obtained precipitate, to prepare a liquid containing latex sensitized with monoclonal antibody Clone8D.

(2) Preparation of Buffer

A buffer was prepared by adding sodium chloride at concentration of 0.9% (wt %) to a 0.1 mol/L Tris buffer (pH8.0) containing bovine serum albumin at a concentration of 0.5% (wt %).

(3) Latex Reagent for Analyzing HMW Adiponectin

A reagent for measuring a human adiponectin antigen used in this Example was prepared as a two-liquid-component reagent composed of the buffer prepared in (2) as the first reagent and the latex sensitized with monoclonal antibody Clone8D prepared in (1) as the second reagent.

Measurement of Adiponectin (1) Measurement of Adiponectin Fractions

To 35 µL of adiponectin fractions from a human serum, 90 µL of the buffer prepared in (2) was added, and the mixtures were allowed to stand at 37° C. for a predetermined period of time. To each of the mixtures, 90 µL of the liquid containing latex sensitized with monoclonal antibody Clone8D prepared in (1) was further added and stirred. After 5 min had passed, the absorbance at a wavelength of 570 nm was measured. A variation in absorbance during this period is regarded as the variation in absorbance (ΔAbs). A standard adiponectin antigen liquid was used to prepare a calibration curve, based on the ΔAbs values and the antigen concentrations. The adiponectin value was calculated from the ΔAbs of each fraction sample using this calibration curve. This measurement was carried out using a HITACHI automated analyzer type 7170.

Simultaneously with this measurement, total adiponectin was measured using the commercially available human adiponectin latex kit (Mitsubishi Kagaku Iatron, Inc.). With respect to the absorbance values measured, for the comparison between the peaks obtained by both reagents, the absorbance values measured using the latex reagent sensitized with monoclonal antibody Clone8D were compensated so that the absorbance values from the No. 109 fraction accorded with each other.

Figure 6:
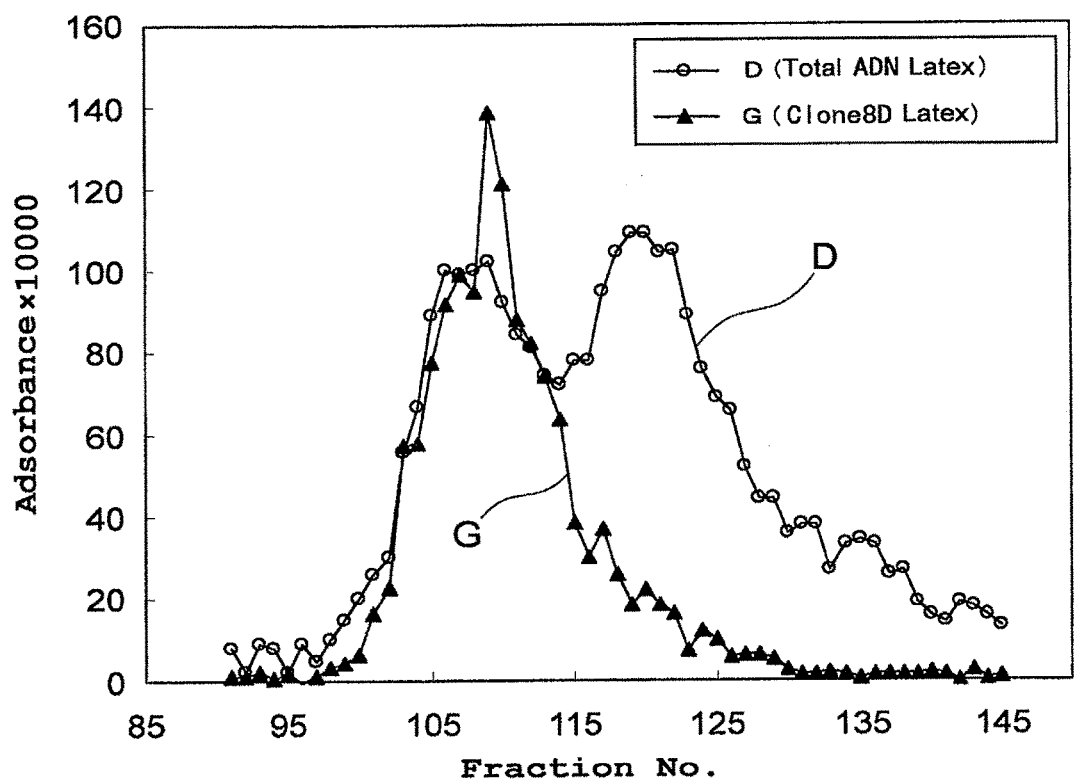
FIG. 6 is a graph showing the results obtained by measuring the amount of adiponectin contained in gel filtration fractions of a human serum sample, using the latex reagent of the present invention prepared using the monoclonal antibody Clone8D of the present invention.

The results are shown in FIG. 6. In FIG. 6, D shows the results of the commercially available human adiponectin latex kit (Mitsubishi Kagaku Iatron, Inc.), and G shows the results of the latex reagent sensitized with antibody Clone8D of the present invention. A latex agglutination reaction specific to HMW was confirmed by measuring the gel filtration fractions of human serum adiponectin using the reagent of the present invention.

INDUSTRIAL APPLICABILITY

The monoclonal antibody of the present invention can be used for the analysis of adiponectin.

Although the present invention has been described with reference to specific embodiments, various changes and modifications obvious to those skilled in the art are possible without departing from the scope of the appended claims.

DEPOSIT NUMBER

Mouse-mouse hybridoma Clone8D was deposited in an International Depositary Authority, the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan), on Mar. 5, 2009. The deposit number is FERM BP-11106.

What is claimed is:

1. A method for producing a monoclonal antibody, the method comprising:
    immunizing a non-human animal with an antigen consisting of high-molecular weight adiponectin purified from human blood, together with an adjuvant;
    producing hybridomas using cells from the immunized non-human animal; and
    selecting a hybridoma which produces a monoclonal antibody which reacts with high-molecular weight adiponectin, does not react with trimeric adiponectin, and does not substantially react with hexameric adiponectin, when analyzed by a latex agglutination method under nonreduced and unheated conditions; wherein the molecular weight of high-molecular weight adiponectin used as the antigen is higher than 670 kDa as determined by gel filtration.

2. The method according to claim 1, the method comprising determining the molecular weight of high-molecular weight adiponectin by gel filtration with Dulbecco's phosphate buffered saline (D-PBS) as a solvent at a speed of 1 mL/minute.

3. A method for producing a monoclonal antibody, the method comprising:
    immunizing a non-human animal with an antigen consisting of high-molecular weight adiponectin having a molecular weight higher than 670 kDa as determined by gel filtration together with an adjuvant, wherein the high-molecular weight adiponectin is purified from human blood;
    producing hybridomas using cells from the immunized non-human animal; and
    selecting a hybridoma which produces a monoclonal antibody which reacts with high-molecular weight adiponectin, does not react with trimeric adiponectin, and does not substantially react with hexameric adiponectin, when analyzed by a latex agglutination method under nonreduced and unheated conditions.

* * * * *